United States Patent
Farkas et al.

(10) Patent No.: US 10,495,566 B2
(45) Date of Patent: Dec. 3, 2019

(54) CIRCUITS, SYSTEMS AND METHODS FOR CORROSION DETECTION

(71) Applicant: DELL PRODUCTS L.P., Round Rock, TX (US)

(72) Inventors: Sandor T. Farkas, Round Rock, TX (US); Wallace H. Ables, Georgetown, TX (US)

(73) Assignee: Dell Products L.P., Round Rock, TX (US)

( * ) Notice: Subject to any disclaimer, the term of this patent is extended or adjusted under 35 U.S.C. 154(b) by 78 days.

(21) Appl. No.: 15/474,549

(22) Filed: Mar. 30, 2017

(65) Prior Publication Data

US 2018/0284011 A1    Oct. 4, 2018

(51) Int. Cl.
    *G01N 17/04*    (2006.01)
    *G01R 17/02*    (2006.01)

(52) U.S. Cl.
    CPC ............ *G01N 17/04* (2013.01); *G01R 17/02* (2013.01)

(58) Field of Classification Search
    CPC ................................ G01N 17/04; G01R 17/02
    USPC ........................................................ 324/700
    See application file for complete search history.

(56) References Cited

U.S. PATENT DOCUMENTS

| 3,378,763 | A | * | 4/1968 | Hastings | ............ | G01N 27/9033 |
|---|---|---|---|---|---|---|
| | | | | | | 324/224 |
| 3,821,642 | A | | 6/1974 | Seymour | | |
| 2004/0027250 | A1 | * | 2/2004 | Hsien | .................. | B25B 23/1425 |
| | | | | | | 340/668 |
| 2005/0269213 | A1 | * | 12/2005 | Steimle | .................. | G01N 17/04 |
| | | | | | | 205/775.5 |
| 2007/0229095 | A1 | * | 10/2007 | Ramgopal | .............. | G01N 17/04 |
| | | | | | | 324/700 |
| 2011/0058298 | A1 | * | 3/2011 | Kuczynski | ........... | H05K 1/0201 |
| | | | | | | 361/103 |
| 2015/0288354 | A1 | * | 10/2015 | Karasawa | ................ | G01K 7/01 |
| | | | | | | 327/83 |

OTHER PUBLICATIONS

Fu et al., "Investigation of Factors That Influence Creep Corrosion on Printed Circuit Boards", Obtained From Internet Nov. 30, 2016, 8 pgs.
Moore et al., "Instrumentation for Measurement of the Effectiveness of Vapor Corrosion Inhibitors", Jun. 1998, 8 pgs.
3M, "Protection of Printed Circuit Boards and Electronic Components From Water and Salt Water by Using 3M Novec Electronic Grade Coatings", Technical Paper, 2014, 4 pgs.

(Continued)

*Primary Examiner* — Jeff W Natalini
(74) *Attorney, Agent, or Firm* — Egan Peterman Enders Huston

(57) ABSTRACT

Circuits, systems and methods are provided that may be implemented using a corrosion sensor that employs a differential bridge circuit layout to detect corrosion events occurring to corrosion-sensitive components such as exposed electronic circuits. In one possible implementation, a detection circuit may be coupled to a corrosion coupon that includes the differential bridge circuit layout, and that is exposed to corrosive conditions such as ambient atmospheric conditions that contain contaminants (e.g., pollutants), humidity, particulates, etc.; as well as varying temperatures.

18 Claims, 8 Drawing Sheets

(56) References Cited

OTHER PUBLICATIONS

Hinds, "Corrosion Monitoring in the Oil & Gas Industry", NPL, Apr. 2010, 41 pgs.
"Solder Mask", Wikipedia, Obtained From Internet Mar. 8, 2017, 2 pgs.
"PCB Solder Mask and Silkscreen", Robot Room, Obtained From Internet Mar. 8, 2017, 9 pgs.
Vidyadhara et al., "Systems and Methods Using Virtual UEFI path for Secure Firmware Handling in Multi-Tenant or Server Information Handling System Environment", U.S. Appl. No. 15/070,639, filed Mar. 15, 2016, DELL:199, 28 pgs.
"Reliability Evaluation of Anti-Corrosion Printed Circuit Board (PCB) Coating", Meiden Review, series No. 166, No. 1, 2016, 3 pgs.
Texas Instruments, "Bridge Measurement Systems", Section 5, Precision Analog Applications Seminar, Obtained From Internet Mar. 4, 2017, 33 pgs.

\* cited by examiner

SECTION A-A

CIRCUITS, SYSTEMS AND METHODS FOR CORROSION DETECTION

FIELD

This invention relates generally to detection circuitry and, more particularly, to corrosion detection circuitry.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Most electronic devices are susceptible to degrading over time from exposure to atmospheric contaminants, pollutants, and humidity, and from residual assembly fluxes and chemicals. Atmospheric contaminate levels vary greatly across geographical regions and environmental control conditions for the installation. Heavily industrialized areas, chemical plant installations, outside free air cooling installations, and high humidity coastal installations have a higher incidence if corrosion related attacks on electronics that results in increased service calls, returns, warranty costs, data loss, fires, user dissatisfaction, etc.

SUMMARY

Disclosed herein are circuits, systems and methods that may be implemented using a corrosion sensor that employs a differential bridge circuit layout to detect corrosion events (e.g., corrosion rate and/or a total amount of corrosion that has occurred) that occur to corrosion-sensitive components such as exposed electronic circuits, e.g., on a continuous basis or during any desired time interval/s. In one embodiment, the disclosed circuits, systems and methods may be implemented using a detection circuit coupled to a corrosion coupon that includes the differential bridge circuit layout, and that is exposed to corrosive conditions, e.g., such as ambient atmospheric conditions that contain contaminants (e.g., pollutants), humidity, particulates, etc.; as well as varying temperatures. In a further embodiment, the disclosed circuits, systems and methods may be implemented to act as an "early warning system" to detect corrosion events occurring to other (e.g., nearby) electrical circuitry or systems exposed at the same time to the same ambient or atmospheric conditions, and to issue a corrosion warning to a user or other entity before proper operation of these circuitry and systems is damaged by the corrosion events. In such a case, a user may react to such a warning by, for example, replacing the exposed circuitry and/or system, cleaning up the environment or otherwise reducing or eliminating corrosive conditions, backing up data to another system before it is lost on an affected system, etc.

In one embodiment, a detection circuit and corrosion coupon may be employed to detect and monitor corrosion events that occur on separate electrical circuitry and electrical systems that are exposed at the same time to the same ambient (e.g., atmospheric or other environment) conditions as the corrosion coupon. Examples of such separate electrical circuitry and systems include, but are not limited to, discrete data center components (e.g., servers, routers, power supplies, display monitors, smoke and fire detectors, etc.) that may share the same ambient and atmospheric conditions as a discrete corrosion coupon that is positioned in the data center separate from the discrete components.

In other embodiments, the disclosed circuitry and methods may be implemented to monitor any other type of environment for the presence of corrosive processes that may be occurring. Examples of such other environments include, but not limited to, interior spaces (e.g., control rooms, equipment rooms, etc.) of facilities such as power sub-stations, chemical or power plants, factories, assembly plants, onshore or offshore drilling rigs, sea-going vessels, cargo containers, etc. Other examples of such environments include, but are not limited to, interior spaces of vehicles such as aircraft, trains, automobiles, trucks, spacecraft, satellites, etc. In yet other embodiments, the disclosed circuitry and methods may be implemented to monitor outdoor environments for the presence of corrosive processes that may be occurring, e.g., in the case where other electrical equipment or systems of concern are exposed to the same weather conditions.

In yet other embodiments, it possible to employ the disclosed circuitry and methods to monitor any environment for the presence of corrosive processes that may be occurring in the absence of any other electrical circuitry or equipment of concern, e.g., such as when evaluating the corrosiveness of a given environment in the absence of other circuitry and/or before placement of other circuitry into the given environment.

In another embodiment, the disclosed circuitry and methods may be implemented to monitor corrosiveness of enclosed internal spaces that house other circuitry. In this regard, a corrosion coupon may be positioned inside the chassis enclosure of any type of device that includes electronic circuitry. Examples of such a device include, but are not limited to, information handling systems (e.g., either non-portable or portable), such as a server, a computer workstation, a notebook computer, a tablet computer, a smart phone, etc. In such an embodiment, corrosion processes may be monitored that are occurring to internal chassis circuitry contained within a chassis enclosure (e.g., such as printed circuit board "PCB" circuitry, processor or microcontroller circuitry, battery circuitry, power supply circuitry, cooling fan system circuitry, display circuitry, etc.).

In another embodiment, aspects of the disclosed circuitry and methods may be implemented to detect corrosion activity in real time using a corrosion coupon with a very thin (e.g., from about 1 mils to about 5 mils, or about 4 mils wide in one exemplary embodiment) filament-type exposed circuit trace that has a high sensitivity to any surface corrosion processes, e.g., such as a circuit trace that exhibits a high reduction in overall thickness due to a corrosion process. In such an embodiment, corrosion activity may be detected in real time by monitoring the change in the electrical resistance of the circuit trace of the corrosion coupon.

In another embodiment, alternate or alternating conductive paths (e.g., conductive traces) of a bridge circuit layout may be covered with a corrosion-resistant material (e.g., solder mask) in a manner that prevents dendritic growth, or electro chemical migration (ECM) between the conductive paths (e.g., traces). In this regard, dendritic growth can happen very quickly in a high humidity or highly contaminated environment, causing a premature failure of a corrosion sensor. Thus, the desired effect to monitor the corrosive nature of the environment to the surface of the conductor may be achieved in this embodiment without creating dendritic growth that shorts out the corrosion sensor.

In one respect, disclosed herein is a corrosion sensor, including: a bridge circuit including four separate electrically conductive paths that include first and second electrically conductive paths coupled together at a first node, and third and fourth electrically conductive paths coupled together at a second node. The first electrically conductive path of the bridge circuit may be coupled to the third electrically conductive path at a third node, and the second electrically conductive path of the bridge circuit may be coupled to the fourth electrically conductive path at a fourth node. The first and fourth electrically conductive paths may be exposed to conditions of an ambient environment, and the second and third electrically conductive paths may be isolated from the conditions of the ambient environment.

In another respect, disclosed herein is a corrosion sensor system, including: a corrosion sensor that includes a bridge circuit including four separate electrically conductive paths that include first and second electrically conductive paths coupled together at a first node, and third and fourth electrically conductive paths coupled together at a second node, where the first electrically conductive path is coupled to the third electrically conductive path at a third node, and the second electrically conductive path is coupled to the fourth electrically conductive path at a fourth node, and where the first and fourth electrically conductive paths are exposed to conditions of an ambient environment, and the second and third electrically conductive paths are isolated from the conditions of the ambient environment. A current source may be electrically coupled to provide a reference current (Iref) across the bridge circuit between the first and second nodes of the corrosion sensor, and a voltage sensor may be electrically coupled to measure the voltage (dV) across the third and fourth nodes of the corrosion sensor.

In another respect, disclosed herein is a method, including: exposing a corrosion sensor to an ambient environment, the corrosion sensor including a bridge circuit including four separate electrically conductive paths that include first and second electrically conductive paths coupled together at a first node, and third and fourth electrically conductive paths coupled together at a second node, where the first electrically conductive path is coupled to the third electrically conductive path at a third node, and the second electrically conductive path is coupled to the fourth electrically conductive path at a fourth node, and where the first and fourth electrically conductive paths are exposed to conditions of an ambient environment, and the second and third electrically conductive paths are isolated from the conditions of the ambient environment; providing a reference current (Iref) across the bridge circuit between the first and second nodes of the corrosion sensor while the corrosion sensor is exposed to the ambient environment; and measuring a voltage (dV) across the third and fourth nodes of the corrosion sensor while Iref is provided across the bridge circuit and while the corrosion sensor is exposed to the ambient environment.

DESCRIPTION OF ILLUSTRATIVE EMBODIMENTS

Figure 1:
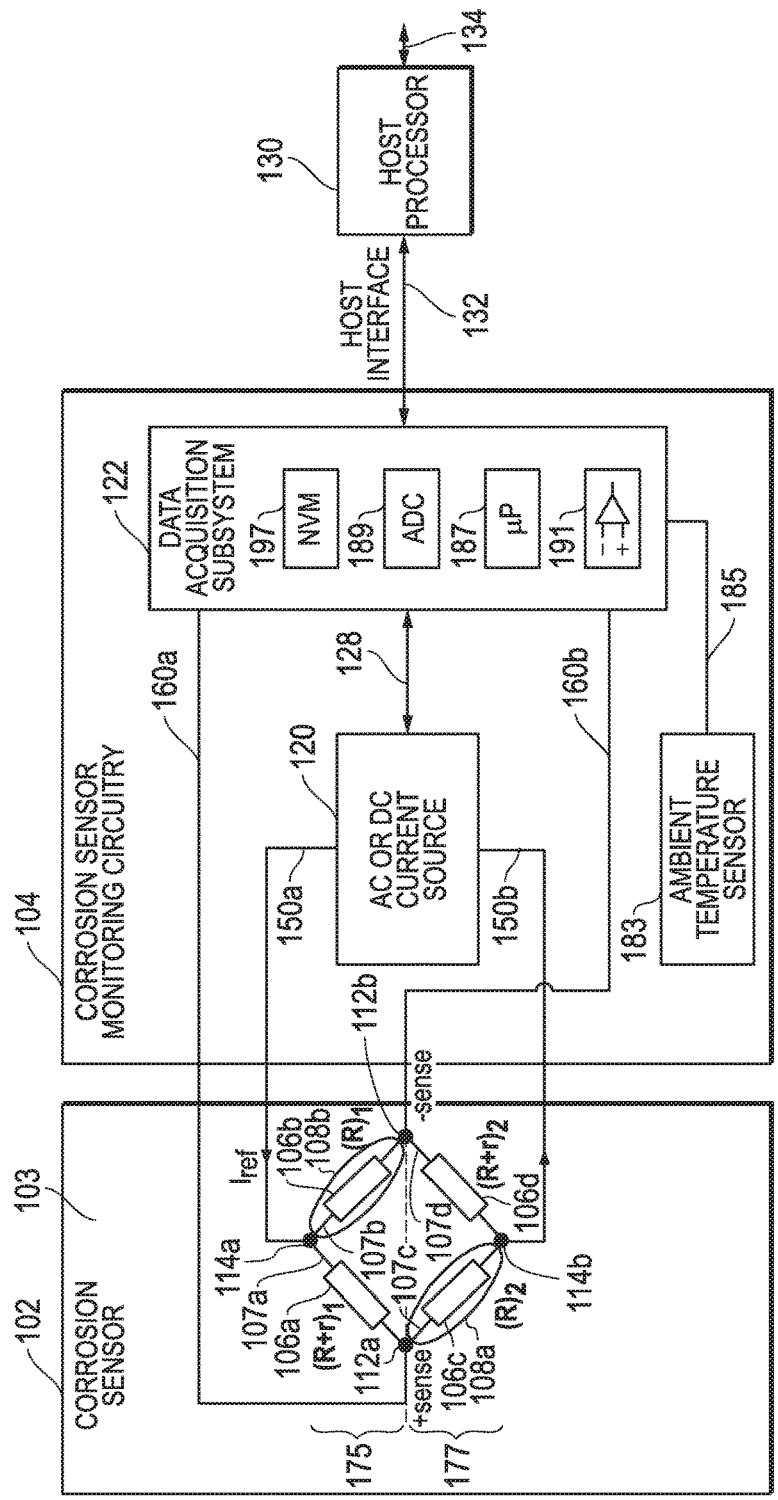
FIG. 1 illustrates a block diagram of a corrosion sensor, corrosion sensor monitoring circuit, and a host programmable integrated circuit according to one exemplary embodiment of the disclosed circuits, systems and methods.

FIG. 1 illustrates a block diagram of a corrosion sensor 102 coupled to corrosion sensor monitoring circuit 104 and a host programmable integrated circuit 130 according to one exemplary embodiment disclosed herein. As shown, corrosion sensor 102 includes electrically conductive paths 107 that in one embodiment be electrically conductive traces (e.g., copper; copper coated with tin, lead, silver, nickel, gold; etc.) that are laid out similar to a Wheatstone bridge architecture on what is in this case a planar substrate 103 such as a printed circuit board (PCB). Particular examples of coated copper traces include, but are not limited to copper traces coated with silver having a nickel under plate coating, and copper traces coated with gold having a nickel under plate coating. In one embodiment, material of conductive path 107 may be selected to be susceptible to corrosion effects from anticipated ambient atmospheric or other ambient environment conditions that contain contaminants (e.g., pollutants such as acid vapors, gases with sulfuric content, any gas, vapor and/or liquid constituent that produces acids or bases in the presence of water, etc.), humidity, particulates (e.g., such as dust, lint, hair, etc., any solid matter that can be carried by the air flow, etc.), combinations thereof, etc. In one exemplary embodiment, material of conductive path 107 may be selected (or tuned) to meet the anticipated ambient environment to which it will be exposed, e.g., a silver conductor is more sensitive to sulfuric acid than is copper, so that silver conductive paths 107 may be selected for use in a highly sulfuric atmosphere. However copper is the most general purpose material and it is commonly used for PCB production, therefore it may be selected for use with PCB-based sensors. In a further embodiment, material of conductive paths 107 may be composed of the same material or materials as one or more conductive materials of separate circuitry and/or device components of interest for which corrosion sensor 102 may be used to monitor for the effects of corrosion. A portion of conductive paths 107 may be configured as a corrosion coupon that is uncovered and exposed to corrosive conditions.

In the embodiment of FIG. 1, a full bridge circuit may be utilized to eliminate the static initial resistance of the a corrosion coupon formed by exposed coupon portions of conductive path 107, providing a low initial offset value that allows higher gain to be set. As shown in FIG. 1, the conductive bridge of corrosion sensor 102 includes a first current tap or node 114a electrically coupled to a first voltage sense tap 112a by a first conductive path 107a forming a resistor 106a and to a second voltage sense tap or node 112b by second conductive path 107b forming a resistor 106b. First voltage sense tap or node 112a is in turn coupled to a second current tap or node 114b by a third conductive path 107c forming a resistor 106c, and second voltage sense tap or node 112b is in turn coupled to the second current tap or node 114b by a fourth conductive path 107d forming a resistor 106d. In this embodiment, branched conductive paths 107a and 107b form a first half 175 of the bridge of sensor 102, and branched conductive paths 107c and 107d form a second half 177 of the bridge of sensor 102. In this embodiment, each of conductive paths 107a, 107b, 107c and 107d have the same geometry (i.e., length and cross section dimensions) as each other, and each of resistors 106a, 106b, 106c and 106d each have the same initial resistance value "R" prior to any occurrence of corrosion.

In one embodiment, branched conductive paths 107a and 107b of the first (upper) bridge half 175 may be routed differentially from the first current tap 114a to voltage sense taps 112a and 112b, and branched conductive paths 107c and 107d of the second (lower) bridge half 177 may be routed differentially from the voltage sense taps 112a and 112b to the second current tap 114b, e.g., as a mirror image or rotated mirror image to each other in which each of the conductive path branches 107a, 107b, 107c and 107d have the same length, cross section dimension, and initial electrical resistance value "R". In this regard, a rotated mirror image is a mirror image along the x-axis, and then mirrored an additional time along the y-axis. Such a differential routing architecture may be implemented to provide improved thermal tracking of the resistors 106 of the bridge of sensor 102, and to provide improved noise rejection, e.g., as compared to uncoupled single-ended serpentine tracks.

As further illustrated in FIG. 1, the entire length of the corrosion-sensitive material of the conductive path branch 107b of the first bridge half of sensor 102 is covered by a corrosion-resistant material 108b to form a first reference path resistance $(R)_1$ that will be isolated from conditions of the surrounding ambient environment and thus unaffected and substantially unchanged by corrosion, while the other corrosion-sensitive conductive path branch 107a of the first bridge half of sensor 102 is left uncovered and therefore exposed to the conditions of the surrounding ambient environment so as to form a first variable sense path resistance $(R+r)_1$ that will increase over time. In this regard, additional incremental resistance "r" increases with time due to corrosion that occurs over time to exposed conductive branch 107a as a result of exposure to the environment surrounding sensor 102. Similarly, the entire length of the corrosion-sensitive material of the conductive path branch 107c of the second bridge half of sensor 102 is covered by corrosion-resistant material 108a to form a reference path resistance $(R)_2$ that will be unaffected and substantially unchanged by corrosion, while the other conductive path branch 107d of the second bridge half of sensor 102 is left uncovered and exposed to the surrounding environment so as to form a variable sense path resistance $(R+r)_2$ that will increase with time due to corrosion that occurs over time as described above. Thus, "R" represents the initial uncorroded (i.e., not corroded) resistance of each conductive path 107, and "r" is the additional incremental resistance that increases with time due to corrosion that occurs over time to uncovered and exposed conductive path branches 107a and 107d as a result of exposure to the environment surrounding sensor 102. In this regard, uncovered and exposed conductive path branches 107a and 107d act as corrosion coupon components of corrosion sensor 102.

Still referring to the embodiment of FIG. 1, each of conductive path branches 107a, 107b, 107c and 107d will have the same initial resistance "R", i.e., before any resistance occurs to uncovered conductive path branches 107a and 107d. This is because both the geometry (length and cross-section dimensions) and conductive material of each of branches 107a, 107b, 107c and 107d is the same as each of the other branches 107. Thus, the value of reference resistance $(R)_1$ will always be the same as the value of reference resistance $(R)_2$, while the value of sense resistance $(R+r)_1$ will always be the same as the value of sense resistance $(R+r)_2$, i.e., since the value of sense resistance $(R+r)_1$ will increase together at the same rate over time due to exposure to the same corrosive conditions. In one embodiment, before exposure to corrosive ambient environment conditions, the initial values of $(R)_1$ and $(R)_2$ may be the same (or may be substantially the same) as the initial values of $(R+r)_1$ and $(R+r)_2$. To illustrate with an example, initial "R" value may be 20 ohms and initial "r" value may be 30 milliohms, such that the initial value of $(R)_1$ and $(R)_2$ is each 20 ohms, while at the same time the initial 20.03 ohms value of each of $(R+r)_1$ and $(R+r)_2$ is substantially the same as the initial 20 ohms value of $(R)_1$ and $(R)_2$.

Full differential operation of bridge 102 may be enabled by virtue of the presence of alternating reference resistances "R" and sense resistances "R+r" in each of the conductive path branches of sensor 102 as shown. This results in a first differential current path that includes sense resistance $(R+r)_1$ and reference resistance $(R)_2$ coupled in series between current tap 114a and current tap 114b, and a second and parallel differential current path that includes reference resistance $(R)_1$ and sense resistance $(R+r)_2$ coupled in series between current tap 114a and current tap 114b. Since each of current taps 114a and 114b is coupled to one of the voltage sense taps 112 by a sense resistance (R+r) and to the other one of voltage sense taps 112 by a reference resistance (R), a differential measurement of instantaneous voltage (dV) that is proportional to corrosion induced resistance increase "r" may be made across voltage sense taps 112a and 112b in a manner as described further below. Full differential operation of sensor 102 not only doubles the dV output signal measured at voltage sense taps 112a and 112b, but also increases noise cancellation.

Corrosion-resistant material 108 may in one embodiment be selected to be resistive (or not susceptible) to corrosion effects from anticipated contacting ambient fluids or ambient atmospheric conditions that contain contaminants, humidity, particulates, combinations thereof, etc. Examples of such corrosion-resistant materials 108 include, but are not limited to, solder mask materials including any film or cured liquid type mask material such as epoxy that are applied onto substrate 103 by silkscreen, liquid photo-imageable solder mask (LPSM of LPI) inks applied onto substrate 103 by silkscreen or spraying, and dry film photo-imageable solder mask (DFSM) materials that are vacuum laminated onto the substrate 103, e.g., LPSM may be selected as a corrosion resistant solder mask for a PCB-based sensor. Solder mask materials such as LPSM and DFSM may be first applied to substrate 103, followed by exposure to a pattern and developing to provide openings for uncovered and exposed circuit portions of sensor 102 that include at least a portion of each of conductive path branches 107a and 107d. After patterning, applied solder mask materials may be thermally cured and/or ultra violet cured in the cast of LPSM or LPI. Besides solder mask materials, other photo imageable materials may be used to protect the reference traces including, but not limited to, conformal coatings or any other impervious coating material, as well as any other coating material that provides corrosion resistance.

In one embodiment, two or more layers of solder mask material/s 108 may be optionally applied to cover each of reference path resistors 106b and 106c of sensor 102 in order to ensure that there are no pin holes or other openings extending from the surrounding environment through the solder mask material to the underlying conductive material. At the same time the opposite sense path resistors 106a and 106d will be exposed and subject to corrosion. Whether coated with one or more layers of solder mask material/s 108, the initial resistance "R" of covered reference path resistors 106b and 106c will remain unchanged or substantially unchanged over time, while the resistance of respective opposing sense path resistors 106a and 106d will increase from an initial resistance "R" to a later resistance of "R+r" over time due to corrosion that occurs with exposure to the surrounding environment.

During operation of the current sensor embodiment of FIG. 1, a constant alternating current (AC) or direct current (DC) reference current (Iref) from current source 120 is passed through the branched conductive paths 107 of sensor 102 between current taps 114a and 114b as shown. At the same time, instantaneous voltage (dV) and optional ambient temperature value 185 is measured across voltage sense taps 112a and 112b by a voltage sensor circuit of data acquisition subsystem 122 of corrosion sensor monitoring circuitry 104. As shown, corrosion sensor monitoring circuitry 104 may include an optional temperature sensor 183 coupled to provide monitored ambient temperature in real time to data acquisition subsystem 122. In one embodiment temperature sensor 183 may be positioned so as to be exposed to (and therefore track) the same ambient temperature to which substrate 103 of corrosion sensor 102 is exposed, e.g., placed in relatively close proximity to substrate 103 or provided within a comment corrosion sensor system housing or chassis. Application of a constant current Iref at a reference voltage (Vref) from source 120 ensures that the resistance of the Iref current conductors (e.g., wires) 150a and 150b are not part of the dV output signal sensed by data acquisition subsystem 122 across voltage sense taps 112a and 112b.

Data acquisition subsystem 122 may include, for example, analog to digital converter (ADC) circuitry 189 configured to receive and convert analog dV measurement signals made using voltage sense conductors (e.g., wires) 160a and 160b to digital dV measurement signals 132 that may be provided from a digital output, e.g., provided via a host interface to a host processor 130 (e.g., central processing unit or other programmable integrated circuit), which in turn may be programmed to further post-process and/or provide monitored corrosion information 134 based on the dV measurement signals that is indicative of an amount of corrosion occurring to exposed conductive paths 107a and 107d. Examples of monitored corrosion information 134 include, but are not limited to, data or other information that is indicative of the amount of corrosion that has occurred or is occurring, a warning that a relatively large amount of cumulative corrosion has occurred (e.g., exceeding a maximum cumulative corrosion threshold value), that a relatively high rate of corrosion is occurring (e.g., exceeding a maximum corrosion rate threshold value), etc. In this regard the monitored corrosion information 134 may be provided to other local or remote components, e.g., for display to a user, storage in non-volatile memory, etc. Data acquisition subsystem 122 may also include an optional amplifier up front depending on the ADC 189 used. Such an amplifier may be configured to implement a low pass filter 191 to low pass filter the incoming dV measurement signals from voltage sense conductors 160a and 160b. In this regard, ADC 189 may in one embodiment be an integrating type ADC to suppress noise further. Additional possible circuitry of data acquisition system 122 may include circuitry configured to detect ADC overload or low signal, and to adjust Iref current accordingly.

Data acquisition subsystem 122 may also include an optional programmable integrated circuit 187 (e.g., such as a microprocessor) coupled to receive digital dV and/or digital temperature data from ADC 189, and may be programmed to perform post-processing of measured dV and temperature data (e.g., such as ambient temperature measurement and temperature compensation processing, determination of corrosion extent, post processing based on monitored ambient temperature in a manner as described further herein, etc.) and/or may be coupled to provide control signals 128. Other components of data acquisition subsystem 122 may include non-volatile memory 197 coupled to microprocessor 187 (e.g., for use with dV and temperature data post-processing and/or corrosion extent determination). Additionally or alternatively, such post-processing (e.g., including temperature compensation) may be performed by a host programmable integrated circuit 130 which may be in one embodiment located physically remote to sensor 102 and corrosion sensor monitoring circuitry 104. In one embodiment, data acquisition subsystem 122 may employ a high impedance that is a few orders of magnitude higher than the source impedance to maintain accuracy (e.g., in one embodiment 1 Mohm (1000 kilohms), or more) to measure dV so as to ensure that the resistance of the voltage sense conductors (e.g., wires) 160a and 160b and corresponding connectors is also ignored, making this embodiment of sensor 102 operate effectively as a Kelvin or 4-wire measurement system in which dV is measured at Iref. Control signals 128 between current source 120 and data acquisition system 122 may be employed to gear shift the current reference depending on sensor resistance, to adjust the current for temperature compensation operation, etc.

While Iref is passed through the bridge of corrosion sensor 102, the resulting voltage dV measured across the bridge at voltage sense taps 112a and 112b at any given time will therefore follow Ohm's law as follows:

$$dV = Vref*[(R+r)/(2R+r)-(R)/(2R+r)]; \text{ where}$$

$$Vref = \tfrac{1}{2}*Iref*(2R+r); \text{ and thus}$$

$$dV = \tfrac{1}{2}*Iref*r$$

Thus, the bridge output voltage dV measured across voltage sense taps 112a and 112b is proportional with the corrosion induced resistance increase "r", and in this embodiment the differential routing architecture of the sensor bridge provides dV as a low noise, low offset, and low impedance signal that allows a large gain to be utilized by the corrosion sensor monitoring circuitry 104. In this regard, corrosion sensor monitoring circuitry 104 may in one embodiment employ a gain in the range of thousands (e.g., a gain greater than about 1000, a gain greater than about 5000, a gain from about 1000 to about 5000, a gain from about 1000 to about 10,000, etc.) depending on the capabilities of the ADC 189. However, these gain values are exemplary only, and lower gain values may also be employed. For example, in one sensor embodiment that employs a relative high conductive trace resistance value "R" (e.g., greater than about 10 ohms, greater than about 20 ohms, from about 10 ohms to about 30 ohms, etc.) and a 20 bit ADC 189 in the corrosion sensor monitoring circuitry 104, the gain value of corrosion sensor monitoring circuitry 104 may be, for example, from about 1 to about 10. Higher gain values (e.g., in the thousands) may be employed with a lower bit ADC of corrosion sensor monitoring circuitry 104. In any case, due to its low noise the disclosed corrosion sensor 102 may be implemented in one embodiment to support large corrosion sensor monitoring circuitry gains, which assists with system implementation.

Post-processing that may be performed by a microprocessor or other programmable integrated circuit of corrosion sensor monitoring circuitry 104 may include normalizing sensor resistance readings. For example, where conductive paths 107 are copper traces, the temperature coefficient of the copper is +0.39% per degree centigrade. This temperature related resistance change may be significant compared to the corrosion related resistance change of variable resistance conductive paths 107a and 107d. Therefore data acquisition subsystem 122 may measure real time ambient temperature 185 (e.g., via ADC 189) and use this measured ambient temperature value to normalize the sensor resistance readings to a constant temperature and compensate for temperature changes of the bridge circuit of the sensor 102 itself. Additionally or alternatively, current source 102 may be adjusted in closed loop fashion to maintain constant load voltage amplitude across the sensor regardless of change in resistances of conductive paths 107 due to temperature. Other post-processing performed by data acquisition subsystem 122 may include averaging and filtering circuitry to remove short term disturbances and leave the long term resistance change component which represents corrosion.

Figure 2:
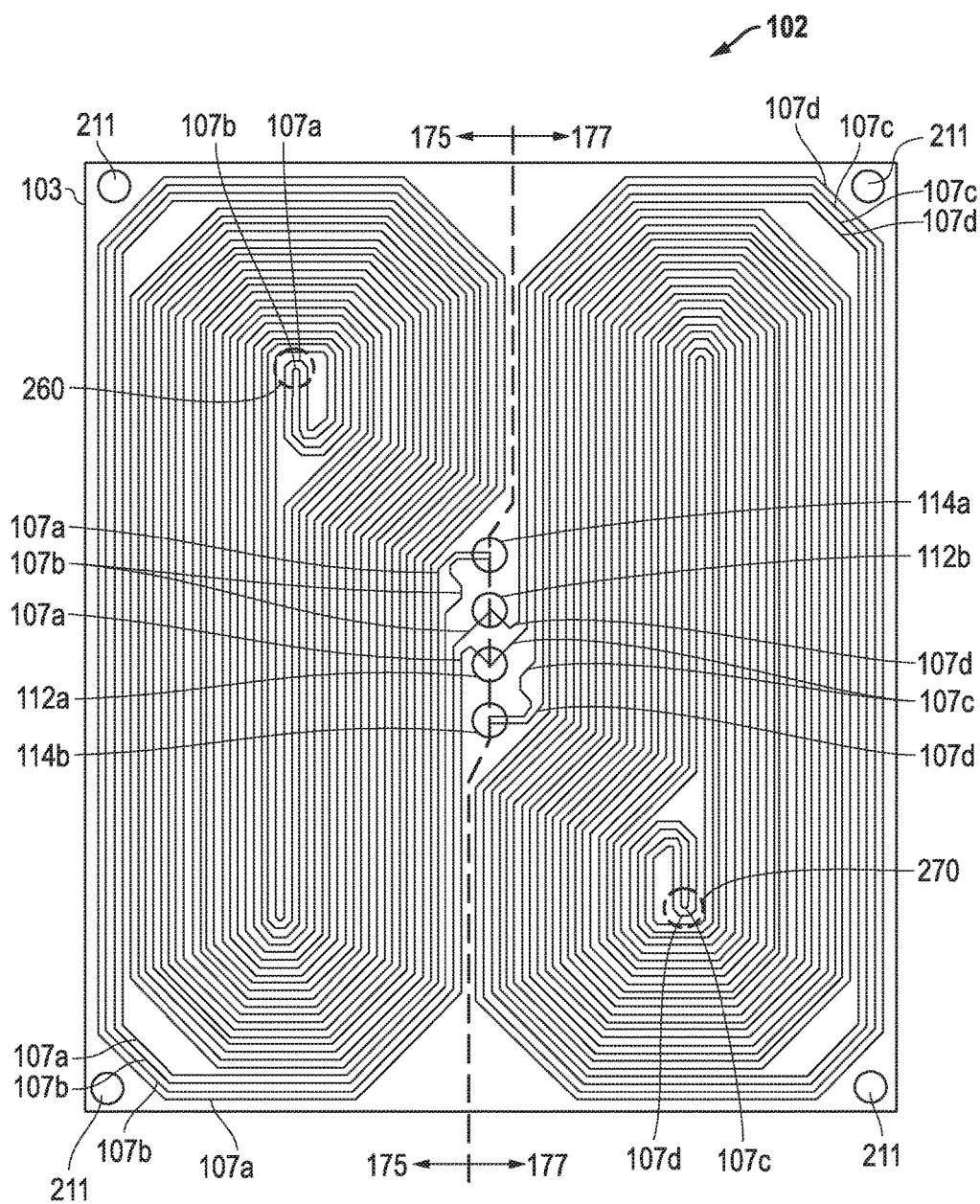
FIG. 2 illustrates an overhead view of an electrically conductive path pattern for a corrosion sensor according to one exemplary embodiment of the disclosed circuits, systems and methods.
Figure 3:
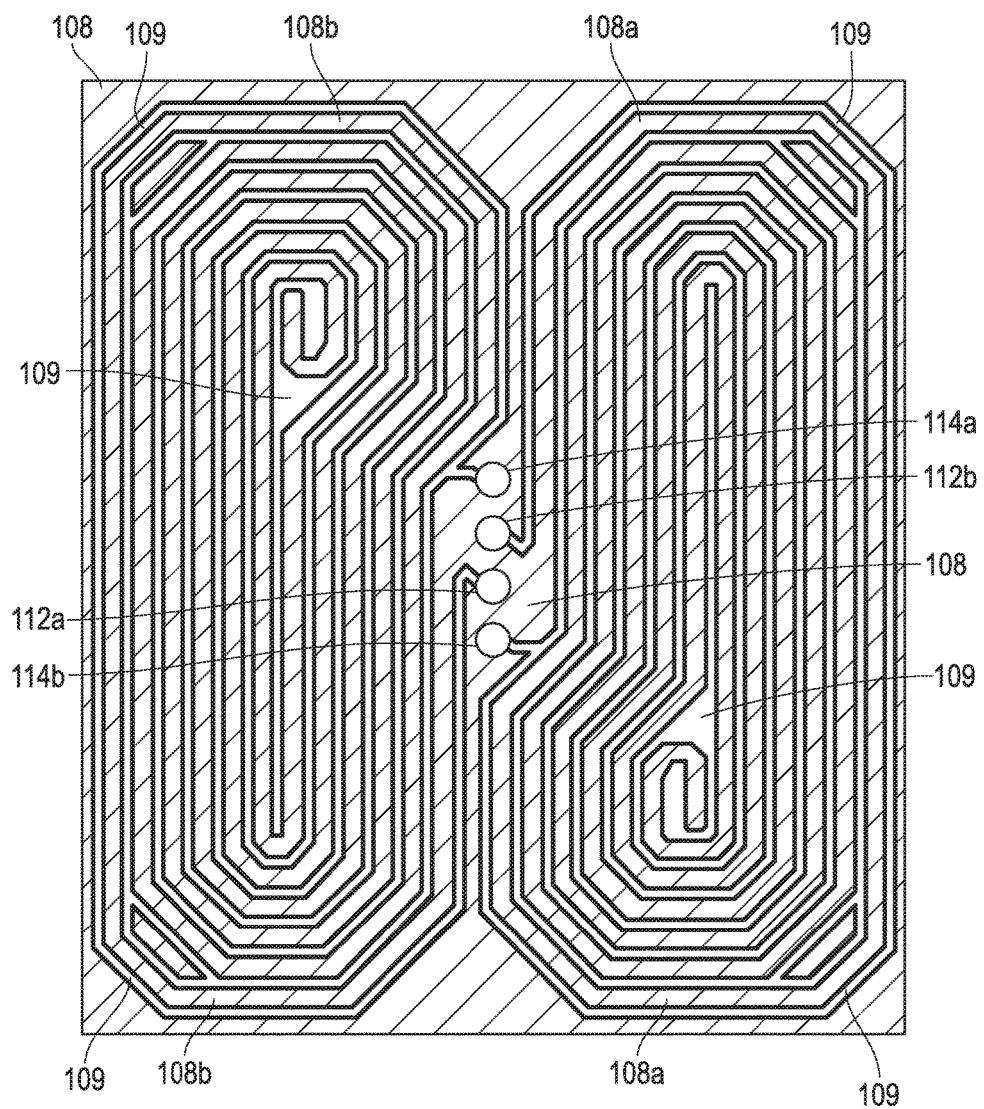
FIG. 3 illustrates an overhead view of a solder mask pattern according to one exemplary embodiment of the disclosed circuits, systems and methods.

For purposes of illustration example only, consider the following example. First, assume all conductive paths 107 of sensor 102 (covered and uncovered) are initially formed of ¼ ounce copper foil (0.35 mils thick) to create 40 inch long and 4 mil wide copper conductive traces 107 in a symmetrical bridge-half pattern on a substrate 103 having outer dimensions of about two inches by two inches (with most of the substrate surface area being used by the pattern of the conductive traces 107), and a shape as illustrated in FIGS. 2-4. In such an example, each of conductive traces 107a, 107b, 107c and 107d may have an initial (uncorroded) resistance of ~20 ohm, i.e., "R"=20 ohm for all conductive paths 107, and incremental resistance "r" of uncovered conductive paths 107a and 107d will initially be 0 ohm (or about 0 ohm) since no corrosion has yet occurred. Next, assume corrosion causes a 1 μ (0.039 mils) thickness loss to occur to the uncovered conductive paths 107a and 107d. This 1 μ copper loss represents ~10% thickness loss (i.e., 0.039 mil loss/4 mil original thickness), which translates to a 10% increase ("r"=~2 ohm) based on the 20 ohm resistance "R", or $(R+r)_1$ and $(R+r)_2$=~22 ohm. Assuming reference current (Iref) applied across current taps 114a and 114b=2 milliamps, the measured dV voltage (according to the relationship dV=½*Iref*r) across voltage sense taps 112a and 112b is ~2 millvolts before gain is added. It will be understood that the above values are exemplary only, provided only for purposes of illustration, and may be greater or lesser values. For example, in another embodiment conductive traces 107a, 107b, 107c and 107d a sensor 102 may have an initial (uncorroded) conductive path resistance of 25 ohm with an initial bridge imbalance of about 40 milliohm.

In one embodiment, given the low bandwidth of the resistance change, heavy filtering may be applied in hardware along with the large gain. It will be understood that the values of conductive path length and thickness (as well as the values of applied current and sensed voltage) given for this example are for purposes of illustration only. Actual values may vary, and may be independently greater or lesser as desired or needed for a given application. For example, for purpose of higher sensitivity, thin copper flash may be used instead of ¼ ounce copper foil. In this regard trace thickness and/or width may be reduced further so as increase resistance and sensitivity. Trace width may also be reduced further to achieve higher density narrower and longer traces in the given area. In such an alternate embodiment, the resulting higher initial resistance increases sensor sensitivity further.

FIG. 2 illustrates an overhead view of one exemplary embodiment of conductive path pattern for a corrosion sensor 102 that includes conductive path branches 107a, 107b, 107c and 107d provided as copper traces (or other layout of suitable conductive material/s) on a PCB 103, e.g., with all traces or conductive paths 107a, 107b, 107c and 107d being length matched with each other. Four pads 114a, 114b, 112a and 112b are the four corners of the bridge of corrosion sensor 102, with outer pads 114a and 114b being the Iref current source tap connections for the sensor 102, and middle pads 112a and 112b being the dV voltage sense tap connections for the sensor 102. The conductive paths 107a and 107b of the first bridge half 175 (upper half of the bridge illustrated in FIG. 1) are shown routed in closely spaced parallel (or bifilar) relationship to each other on the left side of the layout of FIG. 2, and the conductive paths 107c and 107d of the second bridge half 177 (lower half of bridge illustrated in FIG. 1) are shown routed in closely parallel or bifilar relationship to each other on the right side of the layout of FIG. 2. No corrosion-resistant material 108 is yet present in FIG. 2 so that each of conductive path branches 107a, 107b, 107c and 107d are uncovered and completely visible. Optional mounting holes 211 may be provided in substrate 103, e.g., for securing substrate 103 to other system components or to a system chassis. A dashed line in FIG. 2 delineates the separation between the first bridge half 175 and the second bridge half 177.

As shown in FIG. 2, conductive path branches 107a and 107b are laid out in closely parallel side-by-side bifilar fashion in the first bridge half 175 of sensor 102 to create length-matched differential routing between current tap 114a and respective voltage sense taps 112a and 112b so as to better reject noise and improve electromagnetic compatibility (EMC). Additionally, the paths of each given one of conductive path branches 107a and 107b reverses at point 260 to loop back on itself as shown within first bridge half 175 in a manner that acts to cancel out any induced inductive current effects produced by outside electromagnetic fields. Similarly, conductive path branches 107c and 107d are laid out in closely parallel side-by-side bifilar fashion in the second bridge half 177 of sensor 102 to create length-matched differential routing between current tap 114b and respective voltage sense taps 112a and 112b so as to better reject noise and improve electromagnetic compatibility (EMC). In one exemplary embodiment, each of conductive path branches 107a, 107b, 107c and 107d may initially be 4 mil thick conductive copper traces that are laid out with a closely parallel spacing of about 8 mils between inside conductive path pairs and 12 mils between outside conductive path pairs, e.g., to ensure adjacent inside trace pairs 107b of the first bridge half 175 and adjacent inside trace pairs 107c of the second bridge half 177 are covered by solder mask with a typical solder mask positioning tolerance of 2 mils. It will be understood that this spacing is exemplary only and that greater or lesser spacing may be present between adjacent conductive path branches 107. However, closer spacing improves temperature tracking between the parallel conductive paths.

As further shown in FIG. 2, the paths of each given one of conductive path branches 107c and 107d reverses at point 270 to loop back on itself as shown within second bridge half 177 in a manner that acts to cancel out any induced current effects produced by the given conductive path branch on the other conductive path branch. In one exemplary embodiment, the differential pair routing of conductive paths 107 may use 4-8-4-12 geometry, which accommodates a +/−2 mil registration tolerance in a solder mask application (illustrated in FIGS. 3 and 4), and guarantees that the reference traces 107b and 107c are always covered and the sacrificial (sense) traces 107a and 107d are always uncovered.

It will be understood that the particular elongated and symmetrical butterfly shapes of adjacent conductive path branches 107a and 107b of first bridge half 175, and adjacent conductive path branches 107c and 107d of second bridge half 177 shown in FIG. 2 are exemplary only. In this regard, other shapes or geometrical patterns of first bridge half 175 and second bridge half 177 may be laid out symmetrically to each other in order to ensure length matching between the bridge halves and to provide noise cancellation. Examples of other suitable shapes that may be symmetrically employed to lay out the differential conductive path branches 107 of each of first bridge half 175 and second bridge half 177 include, but are not limited to, circular spiral shapes in which the differential conductive path branches 107 loop back on each other from the center of the spiral of each bridge half, zig-zag shapes in which the differential conductive path branches 107 of each bridge half travel back and forth from a first end of the bridge to a second end of the bridge without looping back on each other, etc. In one embodiment, length of conductive paths (e.g., traces) 107 may be maximized in the given available real estate area on PCB 103 for maximum sensitivity.

FIG. 3 illustrates an overhead view of a pattern of one or more solder mask layer/s 108 as it may be formed (e.g., by silkscreen, spraying, vacuum lamination, etc.) over portions of PCB 103 and conductive path trace layers 107 of FIG. 2. Corrosion-resistant material portions 108a and 108b that cover respective conductive path branches 107c and 107b are shown and identified in FIG. 3. Open areas 109 that do not include solder mask material are aligned with respective conductive path branches 107a and 107d. In FIG. 3, position of current taps 114a, 114b and voltage sense taps 112a, 112b of current sensor 102 is also shown relative to solder mask layer/s 108 for reference.

Figure 4A:
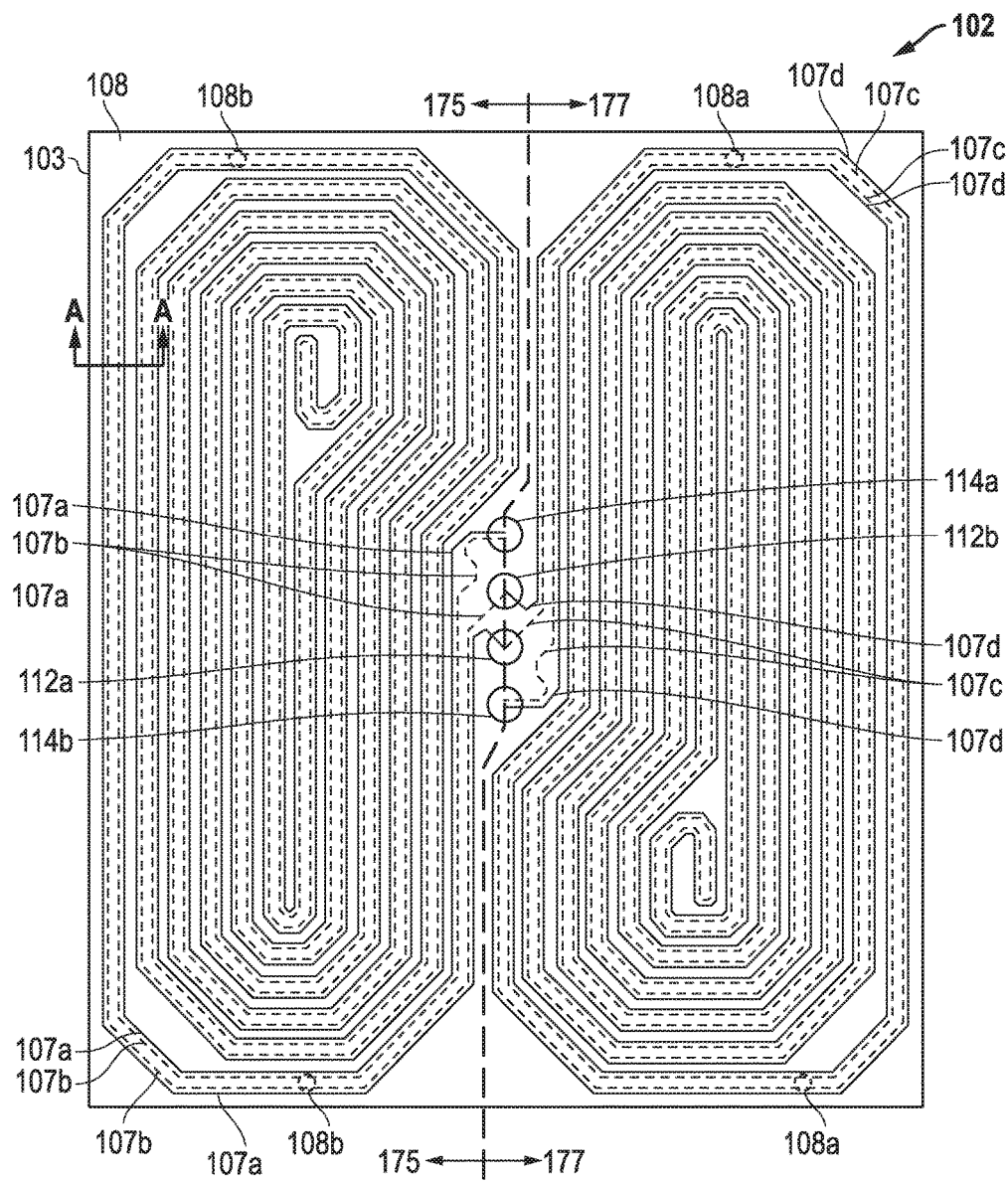
FIG. 4A illustrates a corrosion sensor according to one exemplary embodiment of the disclosed circuits, systems and methods.

FIG. 4A illustrates an overhead view of one exemplary embodiment of a completed corrosion sensor 102 showing corrosion resistant material (e.g., solder mask layer/s) 108 of FIG. 3 aligned with and covering portions of PCB 103 and conductive path trace layers 107 of FIG. 2, e.g., such that the reference conductive path branches 107b and 107c are covered by corrosion-resistant material 108, while the variable resistance conductive paths 107a and 107d are left uncovered by corrosion-resistant material 108 and therefore exposed. Specifically, in FIG. 4A, reference path resistance $(R)_1$ of first bridge half 175 of sensor 102 is provided by conductive path branch 107b (shown as a dashed hidden line) that is covered by corrosion-resistant material portion 108b. Similarly, reference path resistance $(R)_2$ of second bridge half 177 of sensor 102 is provided by conductive path branch 107c (shown as a dashed hidden line) that is covered by corrosion-resistant material portion 108a. Variable sense path resistance $(R+r)_1$ of first bridge half 175 of sensor 102 is provided by uncovered conductive path branch 107a (shown as a solid line), and variable sense path resistance $(R+r)_2$ of second bridge half 177 of sensor 102 is provided by uncovered conductive path branch 107d (shown as a solid line). Conductive voltage sense taps 112a and 112b are uncovered and configured for electrical coupling to suitable voltage sensor circuitry such as data acquisition subsystem 122 via solder connection to voltage sense conductors 160a and 160b, and conductive current taps 114a and 114b are uncovered and configured for electrical coupling to suitable current source circuitry such as current source 120 via solder connection to Iref current conductors 150a and 150b for operation in the manner described in relation to FIG. 1.

Figure 4B:
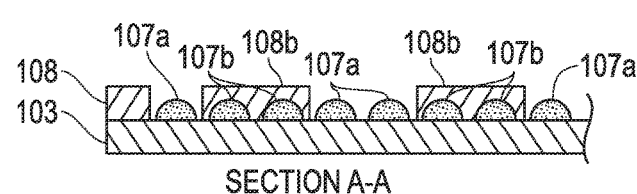
FIG. 4B illustrates a partial cross-sectional view of a corrosion sensor according to one exemplary embodiment of the disclosed circuits, systems and methods.

FIG. 4B is a partial cross-sectional view illustrating section AA from first bridge half 175 of FIG. 4A, showing reference conductive path 107b covered by corrosion-resistant material 108b, and variable resistance conductive path 107a left uncovered by corrosion-resistant material 108.

Figure 5:
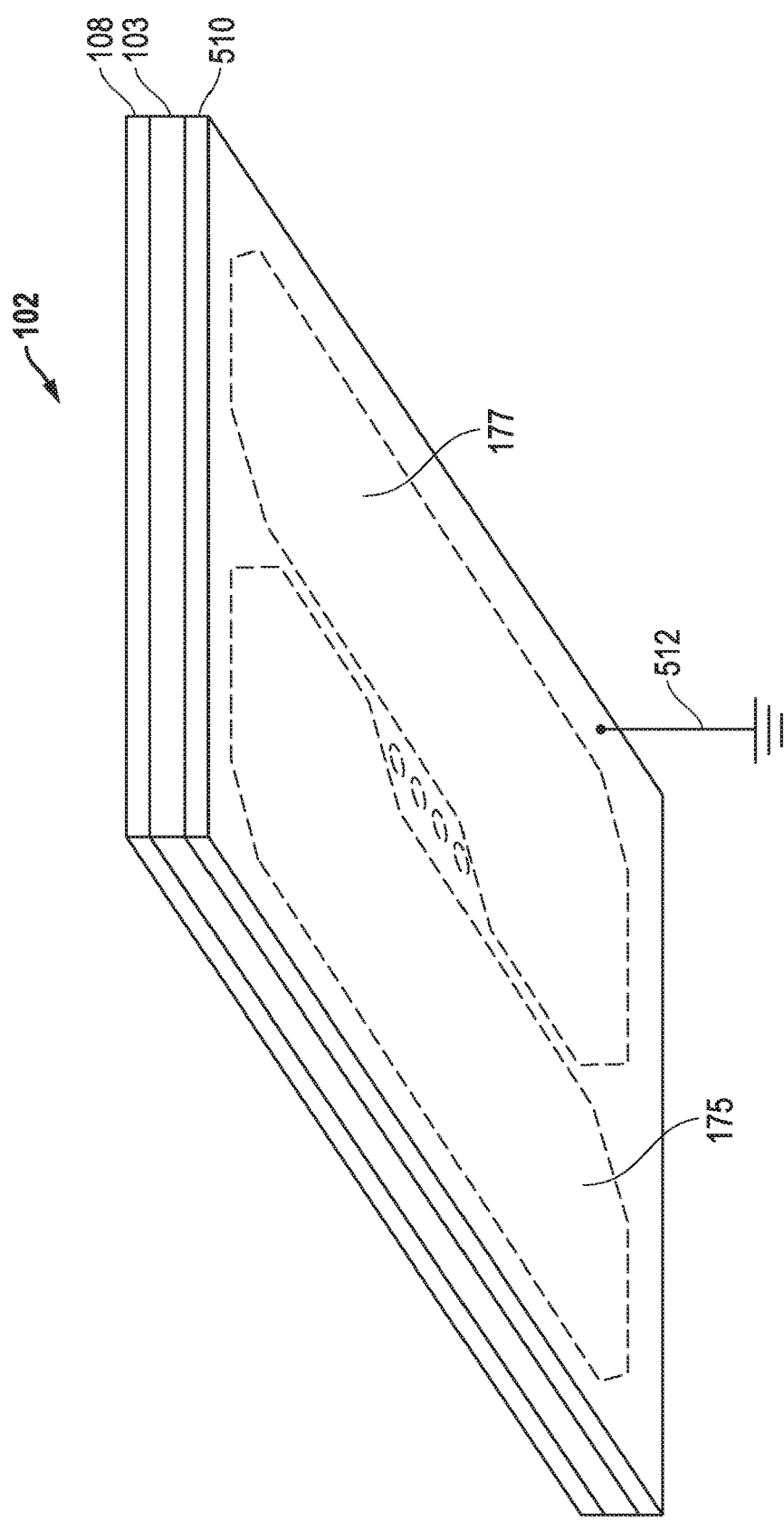
FIG. 5 illustrates an underside perspective view of a corrosion sensor according to one exemplary embodiment of the disclosed circuits, systems and methods.
Figure 6:
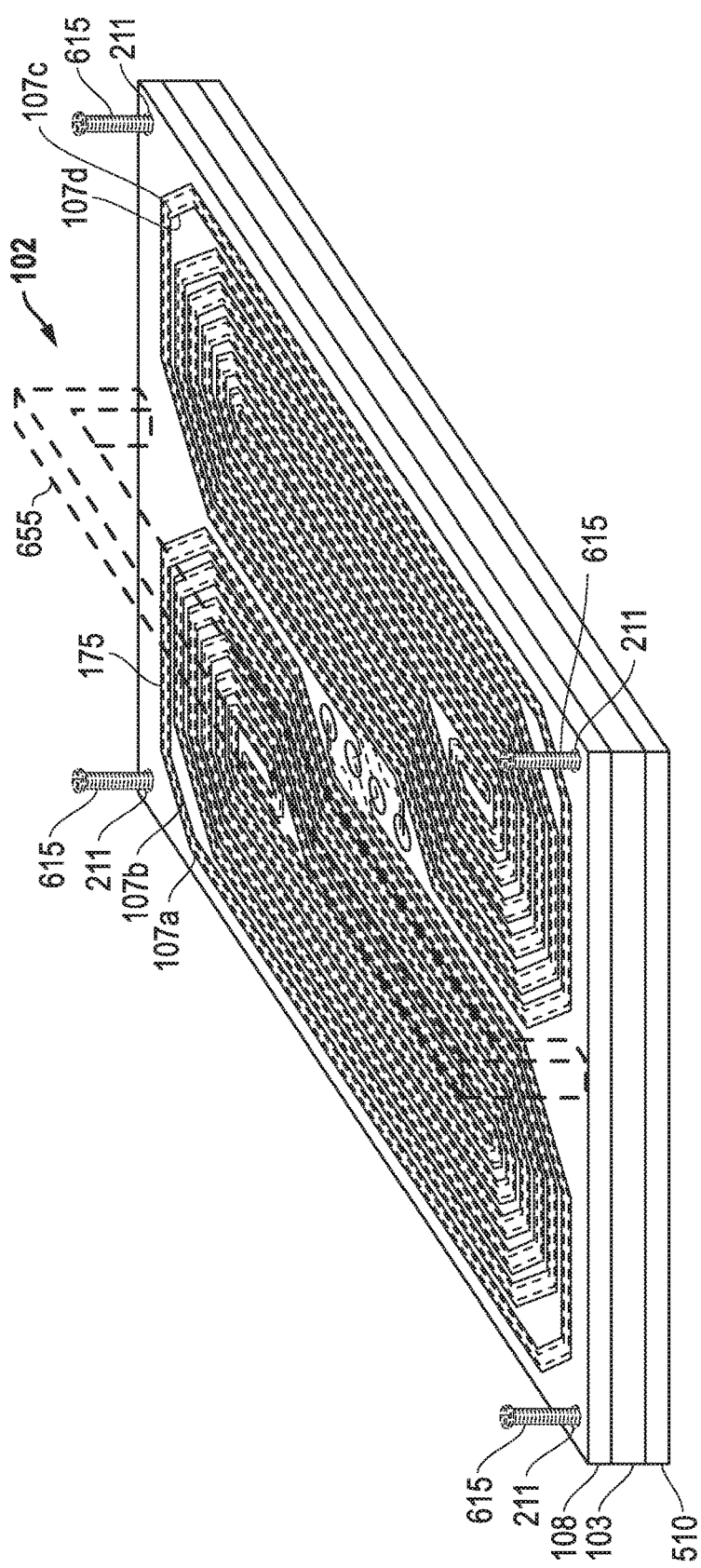
FIG. 6 illustrates an overhead perspective view of a corrosion sensor according to one exemplary embodiment of the disclosed circuits, systems and methods.

FIG. 5 illustrates an underside perspective view showing the lower side of corrosion sensor 102 according to the embodiment of FIG. 4, with the outlines of pads 114a, 114b, 112a and 112b, and first bridge half 175 and second bridge half 177 conductive path circuitry shown in dashed hidden lines since these features are on the opposite upper side of corrosion sensor 102. An optional planar conductive ground plane 510 is illustrated as it may be laminated or otherwise mechanically coupled to the back side or underside of PCB 103 to completely extend beneath the area occupied by conductive path circuitry of sensor 102 on the opposite side of PCB 103 as shown. In such an embodiment, ground plane 510 (e.g., copper foil or other suitable conductive material) may be electrically coupled to circuit ground via conductor 512 as shown for electromagnetic shielding purposes, e.g., to prevent electromagnetic interference emanating from adjacent operating circuitry from being capacitively or inductively coupled into conductive paths 107 of sensor 102 in a manner that adversely affects the accuracy of dV and corrosion measurements by data acquisition subsystem 122 or other suitable voltage sensor circuitry. FIG. 6 illustrates an overhead perspective view showing the upper side of current sensor 102 according to the embodiment of FIG. 4.

In a further embodiment, optional mechanical features may be added to, or positioned relative to, corrosion sensor 102 to manipulate fluid flow patterns around the sensor 102, e.g., such as to disrupt air flow and encourage dust particles to collect in certain areas, e.g., such as on the conductive paths 107 of the bridge of sensor 102. Such mechanical features may be employed, for example, to accelerate corrosion of the uncovered conductive paths 107a and 107d in the presence of humidity, or to better match actual corrosive conditions to which circuitry or other components of concern are exposed. In one exemplary embodiment, optional mechanical features may be employed that extend upward from substrate 103 in adjacent spaced relationship to the conductive path patterns of sensor 102 and/or may be otherwise suspended in adjacent spaced relationship above the conductive path patterns of sensor 102. Specific examples include, but are not limited to, screws that protrude upwards from substrate mounting holes 211, mechanical air dams, an enlarged connector body acting as an air block in the middle of the sensor board, etc. Other specific examples of mechanical features include, but are not limited to, plastic fins or metal fins suspended in spaced relationship above substrate 103 and the conductive path patterns of sensor 102. FIG. 6 illustrates optional screws 615 in dashed outline that may be provided to protrude upwards from substrate mounting holes 211, and an optional fin 655 in dashed outline as it may be suspended in adjacent spaced relationship above the conductive path patterns of sensor 102.

Figure 7:
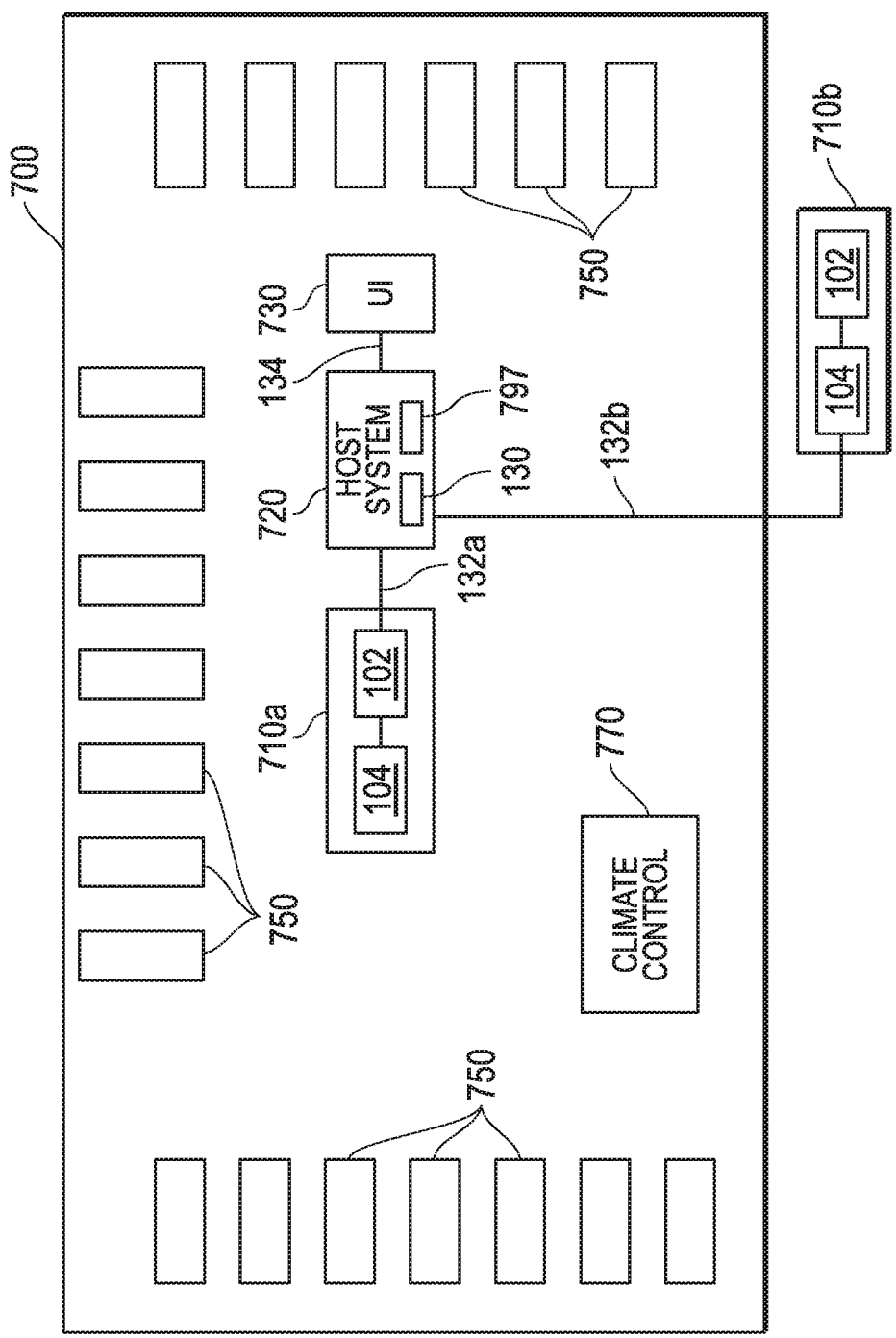
FIG. 7 illustrates stand-alone corrosion sensor systems positioned within and outside of a climate controlled data center room according to one exemplary embodiment of the disclosed circuits, systems and methods.
Figure 8:
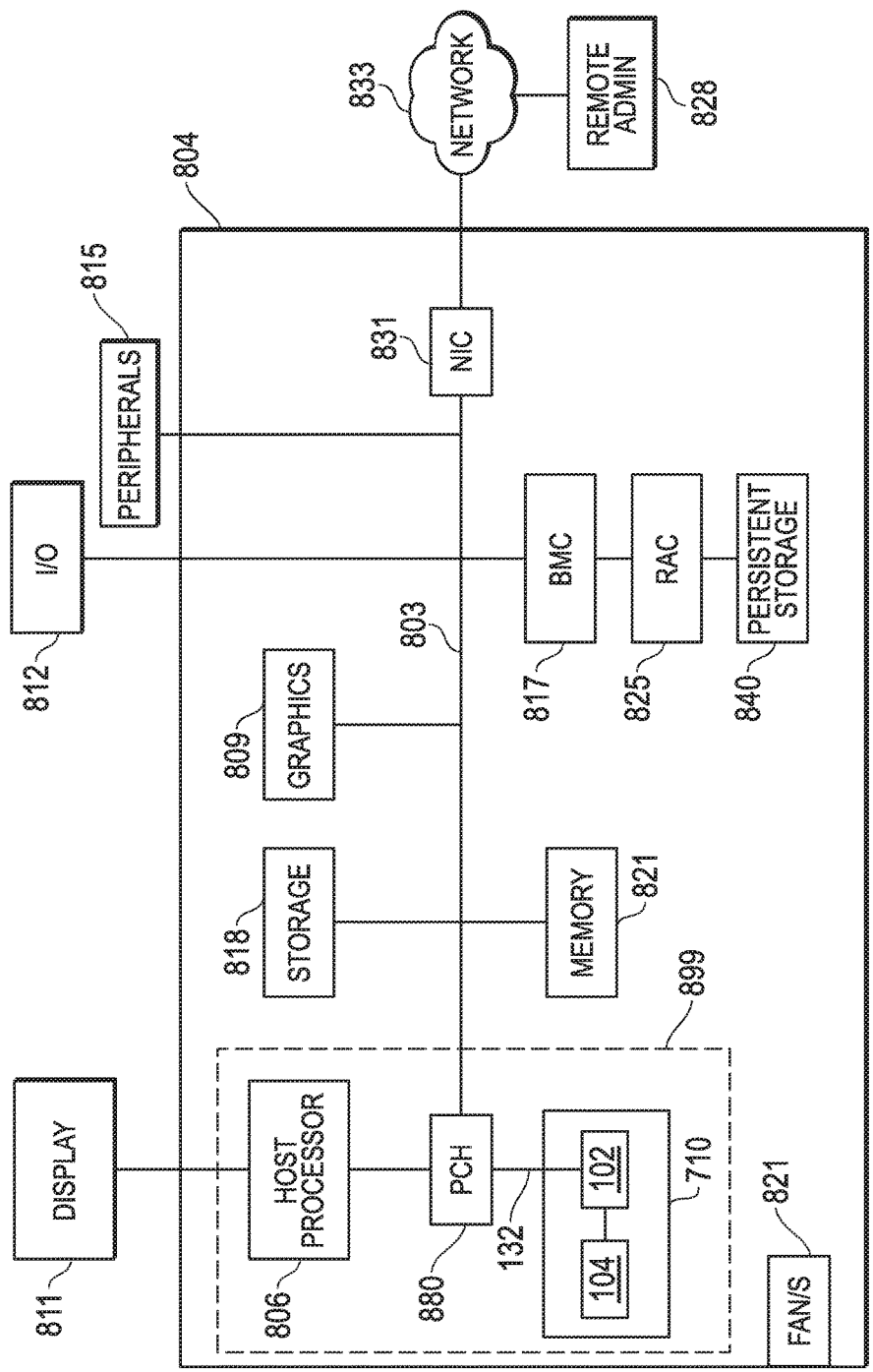
FIG. 8 illustrates a block diagram including an integrated corrosion sensor system according to one exemplary embodiment of the disclosed circuits, systems and methods.

FIGS. 7 and 8 illustrate example implementations of corrosion sensors according to embodiments of the disclosed systems and methods. In this regard, FIG. 7 illustrates a first discrete corrosion sensor system 710a that is positioned as a stand-alone instrument within a climate controlled data center room 700 that houses multiple servers 750 and a climate control system 770. FIG. 7 also illustrates a second discrete corrosion sensor system 710b that is positioned outside climate controlled data center room 700, e.g., in the uncontrolled out-of-doors climate. As shown, each of corrosion sensor systems 710a and 710b may include a corrosion sensor 102 coupled to a corrosion sensor monitoring circuit 104, e.g., such as illustrated and described with respect to FIG. 1.

In FIG. 7, corrosion sensor system 710a is coupled to provide digital dV measurement signals 132a (representative of corrosion occurring within room 700) to a host processor 130 of a corrosion sensor host system 720 that includes non-volatile memory or other suitable storage media 797, and corrosion sensor system 710b is also coupled to provide digital dV measurement signals 132b (representative of corrosion occurring outside of room 700) to a host processor 130 of the corrosion sensor host system 720. A user interface (UI) 730 (e.g., touch display, LED display and keyboard/mouse, etc.) may be coupled to allow host processor 130 to provide monitored corrosion information based on digital dV measurement signals 132a and/or 132b to a user, e.g., in one or more of multiple possible reporting formats. For example, monitored corrosion may be reported as a % corroded value from initial state as an indicator of accumulative damage. Other possible reporting formats include, but are not limited to, display "gas mileage" type numbers, showing momentary values, % per time. Also possible are reporting formats showing long term corrosion trends like seismic data that could be correlated later to chemical spills, etc. Other examples of post-processing that may be performed (e.g., by host processor 130 and/or microprocessor 187) include, but are not limited to, filtering, discarding outlier values due to extreme conditions such as lightning, creating trend lines, curve fitting, etc. Examples of information handling systems that may be employed for corrosion sensor host system 720 are described elsewhere herein, including with regard to FIG. 8. It will be understood that in an alternative embodiment, a host processor 130 and storage 797 may be integrated with sensor 710a into a stand-alone instrument has its own user interface 730.

FIG. 8 illustrates an example implementation of per-unit corrosion monitoring for an individual information handling system (e.g., such as a single network server) using an integrated corrosion sensor system 710 that includes corrosion sensor 102 and corrosion sensor monitoring circuitry 104. In this exemplary embodiment, various internal components of information handling system are contained within a chassis enclosure, such as metal and/or plastic case (e.g., desktop computer tower case, 2U, 3U or 4U rack mount case, notebook computer case, etc.). Examples of internal components include, but are not limited to, at least one host processor or other host programmable integrated circuit 806 (e.g., AMD or Intel-based CPU such as Itanium or any other type of suitable host processing device), one or more buses or communication media 803 (e.g., PCIe bus, USB, SMBus, SATA, other appropriate data buses such as memory bus, etc.), video/graphics hardware 809 (e.g., video adapter or graphics processor unit), storage media 818 (e.g., hard drive/s, solid state drive/s, etc.), system volatile memory (e.g., DRAM) 821, local input/output (I/O) 812, peripherals 815, baseboard management controller (BMC) 817 and remote access controller (RAC) 825 coupled to persistent storage 840. Internal information handling system components may also include a network access card (NIC) 831 that is communicatively coupled to a network 833 (e.g., Internet or corporate intranet) as shown to allow various components of system 804 to communicate with external and/or remote user device/s (include remote administrator information handling system device 828) across network 833. Cooling fan/s 821 may be present to draw in cooling air from outside chassis enclosure 804 and circulate the cooling air through and back out chassis enclosure 804 through cooling vents (not shown). Also not shown is a power supply unit (PSU) that may be present to receive external AC or DC power and distribute/regulate this power to the various internal information handling system components. Further information on information handling system components may be found, for example, in U.S. patent application Ser. No. 15/070,639 filed on Mar. 15, 2016, which is incorporated herein by reference in its entirety for all purposes.

In the embodiment of FIG. 8, integrated corrosion sensor system 710 is coupled to provide digital dV measurement signals 132 (representative of corrosion occurring within chassis enclosure 804) to host processor 806 and/or other programmable integrated circuit such as BMC 817, which in turn may provide monitored corrosion information based on digital dV measurement signals 132 to a local user (e.g., via display 811 and/or to remote administrator device 828 across network 833. In one exemplary embodiment corrosion sensor 719 may be optionally integrated on a PCB of an electrical connector backplane or PCB system board (motherboard) 899, e.g., together with other circuitry such as host processor (e.g., CPU) 806 and/or PCH 880 as shown. In this regard, it is possible in one embodiment that bridge conductive paths 107 may be laid out as conductive traces directly onto a backplane or other system board 899, e.g., such as a motherboard. In another embodiment corrosion sensor 102 may include bridge conductive paths 107 laid out on a separate dedicated PCB.

It will be understood that the embodiments of FIGS. 7 and 8 are exemplary only, and that a corrosion sensor 102 and/or corrosion sensor system 710 may be employed in any other ambient environment to monitor corrosion occurring within a surrounding ambient atmosphere, within the internal ambient fluid (e.g., liquid and/or gaseous) environment of a process vessel, etc.

It will also be understood that corrosion sensor characterization may be performed during development and/or manufacture of a corrosion sensor 102. For example, multiple different samples of a common given configuration of corrosion sensor 102 (i.e., that includes the same particular bridge conducive path material and circuit layout geometry) may be exposed to respective different levels or amounts of corrosion, e.g., by exposing each different sample corrosion sensor 102 to a common corrosive environment for a different amount of time. The resulting resistance change ("r") measured for each different corrosion sensor sample (i.e., that has a unique cumulative corrosion amount that is different from the other samples) may be logged or recorded. Each corrosion sensor may then be physically cut and cross sectioned to observe and visually, physically or otherwise quantitatively measure the actual extent of corrosion to occur to exposed bridge conductive paths of the particular sensor. The measured resistance change "r" for each corrosion sensor sample 102 may then be correlated to the corresponding measured quantitative corrosion extent in order to derive correlation data between measured "r" values and corrosion extent, e.g., such as a lookup table of "r" values versus corrosion extent and/or an x-y plot of "r" values versus corrosion extent. Examples of corrosion extent values may include, for example, weight loss, reduced cross-section area, etc. The derived corrosion correlation data may then be saved in non-volatile memory or storage of an information handling system 804 or corrosion sensor host system 720 for use with a field-deployed corrosion sensor 102, e.g., host processor 130 and/or microprocessor 187 may determine an extent of corrosion occurring to conductive paths 107a and 107d based on resistance changed values "r" calculated from the measured dV information. In a further embodiment, this correlation data may then be used to set a warning trigger or threshold measured resistance value "r" (that correlates to a selected threshold corrosion level), above which a host processor 130 or other suitable programmable integrated circuit may produce a corrosion warning 134, e.g., such as message or display to a user or administrator, as a warning saved in an event log, etc.

In yet another possible embodiment, a corrosion sensor 102 may be alternately employed to evaluate effectiveness of different corrosion resistant treatments at preventing or slowing down corrosion. For example, a first test corrosion sensor 102 may be configured as a corrosion coupon in which exposed corrosion-sensitive conductive paths (e.g., copper traces) 107a and 107d are covered or coated with corrosion resistant coatings or materials to be tested, while the other corrosion-resistant conductive paths 107b and 107c remain coated with a known corrosion-resistant material. A second corrosion sensor 102 having uncoated (and exposed) conductive paths (e.g., copper traces) 107a and 107d with corrosion-resistant conductive paths 107b and 107c may be provided as a control corrosion coupon that is placed in the same ambient environment as the first corrosion sensor 102. In such an embodiment, the difference in corrosion that occurs between the treated corrosion coupon of the first sensor 102 and the untreated corrosion coupon of the second sensor 102 may be compared to gauge the corrosion-resisting effectiveness of the particular corrosion resistant coatings or materials under test.

In a further alternative embodiment, at least two separate and different first and second corrosion sensor circuits 102 may be laid-out or otherwise provided on a single substrate or coupon. In such an embodiment, a first test corrosion sensor 102 on the common coupon may be configured with exposed conductive paths (e.g., copper traces) 107a and 107d that are covered or coated with corrosion resistant coatings or materials to be tested, while the other corrosion-resistant conductive paths 107b and 107c remain coated with a known corrosion-resistant material. A second corrosion sensor 102 of the same coupon may have uncoated and exposed conductive paths (e.g., copper traces) 107a and 107d with corrosion-resistant conductive paths 107b and 107c. In such an embodiment, it may be possible to monitor the difference in corrosion rates between the coated and uncoated sensors 102, which is very useful in characterizing a user or field corrosive environment and for selecting an optimum protective measure/corrective action.

It will be understood that one or more of the tasks, functions, or methodologies described herein for an information handling system or component thereof (e.g., including those described herein for components 122, 130, 806, 809, 817, 187, etc.) may be implemented by circuitry and/or by a computer program of instructions (e.g., computer readable code such as firmware code or software code) embodied in a non-transitory tangible computer readable medium (e.g., optical disk, magnetic disk, non-volatile memory device, etc.), in which the computer program comprising instructions are configured when executed (e.g., executed on a programmable integrated circuit such as CPU, controller, microcontroller, microprocessor, ASIC, etc. or executed on a programmable logic device "PLD" such as FPGA, complex programmable logic device "CPLD", etc.) to perform one or more steps of the methodologies disclosed herein. In one embodiment, a group of such processors and PLDs may be programmable integrated circuits selected from the group consisting of CPU, controller, microcontroller, microprocessor, FPGA, CPLD and ASIC. The computer program of instructions may include an ordered listing of executable instructions for implementing logical functions in an information handling system or component thereof. The executable instructions may include a plurality of code segments operable to instruct components of an information handling system to perform the methodologies disclosed herein. It will also be understood that one or more steps of the present methodologies may be employed in one or more code segments of the computer program. For example, a code segment executed by the information handling system may include one or more steps of the disclosed methodologies. It will be understood that a programmable integrated circuit may be configured to execute or otherwise be programmed with software, firmware, logic, and/or other program instructions stored in one or more non-transitory tangible computer-readable mediums (e.g., example, data storage devices, flash memories, random access memories, read only memories, programmable memory devices, reprogrammable storage devices, hard drives, floppy disks, DVDs, CD-ROMs, and/or any other tangible data storage mediums) to perform the operations, tasks, functions, or actions described herein for the disclosed embodiments.

For purposes of this disclosure, an information handling system may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an information handling system may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, touch screen and/or a video display. The information handling system may also include one or more buses operable to transmit communications between the various hardware components.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed circuits, systems and methods may be utilized in various combinations and/or independently. Thus the invention is not limited to only those combinations shown herein, but rather may include other combinations.

What is claimed is:

1. A corrosion sensor, comprising:
   a bridge circuit comprising four separate electrically conductive paths that include first and second electrically conductive paths coupled together at a first node, and third and fourth electrically conductive paths coupled together at a second node;
   where the first electrically conductive path is coupled to the third electrically conductive path at a third node, and the second electrically conductive path is coupled to the fourth electrically conductive path at a fourth node;
   where the first and fourth electrically conductive paths are exposed to conditions of an ambient environment, and the second and third electrically conductive paths are isolated from the conditions of the ambient environment; and
   where the first and second electrically conductive paths are routed in side-by-side parallel bifilar relationship to each other to form a first half of the bridge circuit, and where the third and fourth electrically conductive paths are routed in side-by-side parallel bifilar relationship to each other to form a second half of the bridge circuit that is separate from the first half of the bridge circuit; and
   where each of the side-by-side parallel first and second electrically conductive paths are routed to reverse direction to loop back on itself within the first half of the bridge circuit such that a portion of the first electrically conductive path is routed in side-by-side parallel bifilar relationship with itself with no second electrically conductive path portion therebetween within the first half of the bridge circuit, and such that a portion of the second electrically conductive path is routed in side-by-side parallel bifilar relationship with itself with no first electrically conductive path portion therebetween within the first half of the bridge circuit; where each of the side-by-side parallel third and fourth electrically conductive paths are routed to reverse direction to loop back on itself within the second half of the bridge circuit such that a portion of the third electrically conductive path is routed in side-by-side parallel bifilar relationship with itself with no fourth electrically conductive path portion therebetween within the second half of the bridge circuit, and such that a portion of the fourth electrically conductive path is routed in side-by-side parallel bifilar relationship with itself with no third electrically conductive path portion therebetween within the second half of the bridge circuit; and where the conductive paths of the first half of the bridge circuit are laid out separately and symmetrically to the conductive paths of the second half of the bridge circuit.

2. The sensor of claim 1, where each of the four separate electrically conductive paths is an electrically conductive trace that is composed of the same electrically conductive material as each of the other four separate electrically conductive paths; where each of the four separate electrically conductive paths is an electrically conductive trace having the same length and cross section dimensions as each of the other four separate electrically conductive paths; and where each of the first and second nodes are separate current taps passing a constant current therebetween, and each of the third and fourth nodes are voltage nodes exhibiting an instantaneous voltage therebetween.

3. The sensor of claim 1, where each of the four separate electrically conductive paths is disposed on a first side of a planar substrate that has opposing first and second sides; where the second and third electrically conductive paths are covered by solder mask material; and where the first and fourth electrically conductive materials are not covered by the solder mask material.

4. The sensor of claim 3, further comprising a planar electrically conductive ground plane, the ground plane being mechanically coupled to the second side of the planar substrate to completely extend opposite the area occupied by the bridge circuit on the first side of the planar substrate.

5. The sensor of claim 3, where the planar substrate is a printed circuit board (PCB); and where each of the four separate electrically conductive paths is an electrically conductive trace that comprises at least one of copper or silver.

6. The sensor of claim 3, where the planar substrate is a PCB backplane or system board of an information handling system that includes other information handling system circuitry.

7. The sensor of claim 1, where the first, second, third and fourth electrically conductive paths have the same length as each other; where the first and third electrically conductive paths are coupled together at the third node to form a first differential current path between the first node and the second node; and where the second and fourth electrically conductive paths are coupled together at the fourth node to form a second differential current path between the first node and the second node, the first and second differential current paths having the same length as each other.

8. The sensor of claim 1, where each of the four separate electrically conductive paths is disposed on a substrate; where the sensor further comprises one or more mechanical features that are disposed in adjacent spaced relationship relative to the electrically conductive paths of the corrosion sensor to manipulate fluid flow patterns to disrupt air flow around selected areas of the sensor; and where the mechanical features comprise at least one fin suspended in adjacent spaced relationship to the electrically conductive paths of the bridge circuit.

9. A corrosion sensor system, comprising:
a corrosion sensor that comprises a bridge circuit comprising four separate electrically conductive paths that include first and second electrically conductive paths coupled together at a first node, and third and fourth electrically conductive paths coupled together at a second node, where the first electrically conductive path is coupled to the third electrically conductive path at a third node, and the second electrically conductive path is coupled to the fourth electrically conductive path at a fourth node, and where the first and fourth electrically conductive paths are exposed to conditions of an ambient environment, and the second and third electrically conductive paths are isolated from the conditions of the ambient environment;
a current source electrically coupled to provide a reference current (Iref) across the bridge circuit between the first and second nodes of the corrosion sensor; and
a voltage sensor electrically coupled to measure the voltage (dV) across the third and fourth nodes of the corrosion sensor;
where the first and second electrically conductive paths are routed in side-by-side parallel bifilar relationship to each other to form a first half of the bridge circuit, and where the third and fourth electrically conductive paths are routed in side-by-side parallel bifilar relationship to each other to form a second half of the bridge circuit that is separate from the first half of the bridge circuit; and
where the corrosion sensor system is contained within a chassis enclosure of an information handling system; where each of the four separate electrically conductive paths is disposed on a first side of a planar substrate that has opposing first and second sides; where the second and third electrically conductive paths are covered by solder mask material; where the first and fourth electrically conductive materials are not covered by the solder mask material; where each of the side-by-side parallel first and second electrically conductive paths are routed to reverse direction to loop back on itself within the first half of the bridge circuit such that a portion of the first electrically conductive path is routed in side-by-side parallel bifilar relationship with itself with no second electrically conductive path portion therebetween within the first half of the bridge circuit, and such that a portion of the second electrically conductive path is routed in side-by-side parallel bifilar relationship with itself with no first electrically conductive path portion therebetween within the first half of the bridge circuit; where each of the side-by-side parallel third and fourth electrically conductive paths are routed to reverse direction to loop back on itself within the second half of the bridge circuit such that a portion of the third electrically conductive path is routed in side-by-side parallel bifilar relationship with itself with no fourth electrically conductive path portion therebetween within the second half of the bridge circuit, and such that a portion of the fourth electrically conductive path is routed in side-by-side parallel bifilar relationship with itself with no third electrically conductive path portion therebetween within the second half of the bridge circuit; and where the planar substrate is a PCB backplane or system board of an information handling system that includes other information handling system circuitry.

10. The system of claim 9, where the voltage sensor is coupled to provide measured dV to at least one programmable integrated circuit; and where the at least one programmable integrated circuit has a digital signal output to provide digital dV measurement signals corresponding to the dV measured across the third and fourth nodes of the corrosion sensor.

11. The system of claim 10, further comprising a temperature sensor coupled to the at least one programmable integrated circuit, the temperature sensor being positioned to sense an ambient temperature of the environment to which the bridge circuit is exposed and to provide the sensed ambient temperature to the programmable integrated circuit; and where the at least one programmable integrated circuit is coupled to at least one of:
control the current source to vary Iref based on the sensed ambient temperature, or
normalize sensor resistance readings based on the measured dV to a constant temperature to compensate for temperature changes of the bridge circuit.

12. The system of claim 10, where the at least one programmable integrated circuit is programmed to determine monitored corrosion information that is indicative of an amount of corrosion occurring to the exposed first and fourth electrically conductive paths based on the digital dV measurement signals; and provide the monitored corrosion information to a user.

13. A method, comprising:
exposing a corrosion sensor to an ambient environment, the corrosion sensor including a bridge circuit comprising four separate electrically conductive paths that include first and second electrically conductive paths coupled together at a first node, and third and fourth electrically conductive paths coupled together at a second node, where the first electrically conductive path is coupled to the third electrically conductive path at a third node, and the second electrically conductive path is coupled to the fourth electrically conductive path at a fourth node, and where the first and fourth electrically conductive paths are exposed to conditions of an ambient environment, and the second and third electrically conductive paths are isolated from the conditions of the ambient environment;
providing a reference current (Iref) across the bridge circuit between the first and second nodes of the corrosion sensor while the corrosion sensor is exposed to the ambient environment; and
measuring a voltage (dV) across the third and fourth nodes of the corrosion sensor while Iref is provided across the bridge circuit and while the corrosion sensor is exposed to the ambient environment;
where the first and second electrically conductive paths are routed in side-by-side parallel bifilar relationship to each other to form a first half of the bridge circuit, and where the third and fourth electrically conductive paths are routed in side-by-side parallel bifilar relationship to each other to form a second half of the bridge circuit that is separate from the first half of the bridge circuit; and
where each of the side-by-side parallel first and second electrically conductive paths are routed to reverse direction to loop back on itself within the first half of the bridge circuit such that a portion of the first electrically conductive path is routed in side-by-side parallel bifilar relationship with itself with no second electrically conductive path portion therebetween within the first half of the bridge circuit, and such that a portion of the second electrically conductive path is routed in side-by-side parallel bifilar relationship with itself with no first electrically conductive path portion therebetween within the first half of the bridge circuit;

where each of the side-by-side parallel third and fourth electrically conductive paths are routed to reverse direction to loop back on itself within the second half of the bridge circuit such that a portion of the third electrically conductive path is routed in side-by-side parallel bifilar relationship with itself with no fourth electrically conductive path portion therebetween within the second half of the bridge circuit, and such that a portion of the fourth electrically conductive path is routed in side-by-side parallel bifilar relationship with itself with no third electrically conductive path portion therebetween within the second half of the bridge circuit; and where the conductive paths of the first half of the bridge circuit are laid out separately and symmetrically to the conductive paths of the second half of the bridge circuit.

14. The method of claim 13, further comprising:

positioning a stand-alone corrosion sensor system within the ambient environment, the stand-alone corrosion sensor system comprising the corrosion sensor, a current source electrically coupled to provide the reference current (Iref) as a constant current across the bridge circuit between the first and second nodes of the corrosion sensor, and a voltage sensor electrically coupled to measure the voltage (dV) across the third and fourth nodes of the corrosion sensor; and converting the measured dV to digital dV measurement signals;

determining monitored corrosion information that is indicative of an amount of corrosion occurring to the exposed first and fourth electrically conductive paths based on the digital dV measurement signals; and providing the monitored corrosion information to a local or remote system user.

15. The method of claim 13, further comprising:

operating a corrosion sensor system while it is contained within a chassis enclosure of an information handling system and exposed to the ambient environment within the chassis enclosure, the corrosion sensor system comprising the corrosion sensor, a current source electrically coupled to provide the reference current (Iref) across the bridge circuit between the first and second nodes of the corrosion sensor, and a voltage sensor electrically coupled to measure the voltage (dV) across the third and fourth nodes of the corrosion sensor;

converting the measured dV to digital dV measurement signals; and determining monitored corrosion information that is indicative of an amount of corrosion occurring to the exposed first and fourth electrically conductive paths based on the digital dV measurement signals; and providing the monitored corrosion information to a host programmable integrated circuit of the information handling system that is contained within the chassis enclosure; and providing the monitored corrosion information from the host programmable integrated circuit to a local user of the information handling system or to a remote system user that is communicatively coupled to the host programmable integrated circuit of the information handling system.

16. The method of claim 13, further comprising sensing an ambient temperature of the environment to which the bridge circuit is exposed; and at least one of controlling a current source to vary Iref based on the sensed ambient temperature, or to normalize sensor resistance readings based on the measured dV to a constant temperature to compensate for temperature changes of the bridge circuit.

17. The method of claim 13, further comprising converting the measured dV to digital dV measurement signals, and determining monitored corrosion information that is indicative of an amount of corrosion occurring to the exposed first and fourth electrically conductive paths based on the digital dV measurement signals; and providing a warning to user if the monitored corrosion information indicates that a maximum threshold amount of corrosion to the exposed first and fourth electrically conductive paths has been exceeded, and/or if the monitored corrosion information indicates that a maximum corrosion rate to the exposed first and fourth electrically conductive paths has been exceeded.

18. The method of claim 13, further comprising characterizing the corrosion sensor by:

exposing multiple different corrosion sensors of the same corrosion sensor configuration to different respective amounts of corrosion occurring in the ambient environment, each of the corrosion sensors including a bridge circuit comprising four separate electrically conductive paths that include first and second electrically conductive paths coupled together at a first node, and third and fourth electrically conductive paths coupled together at a second node, where the first electrically conductive path is coupled to the third electrically conductive path at a third node, and the second electrically conductive path is coupled to the fourth electrically conductive path at a fourth node, and where the first and fourth electrically conductive paths are exposed to conditions of an ambient environment, and the second and third electrically conductive paths are isolated from the conditions of the ambient environment;

providing a reference current (Iref) across the bridge circuit between the first and second nodes of each corrosion sensor while each corrosion sensor is exposed to a different amount of corrosion than the other corrosion sensors; and measuring a voltage (dV) across the third and fourth nodes of each of the corrosion sensor while Iref is provided across the bridge circuit and while each corrosion sensor is exposed to a different amount of corrosion than the other corrosion sensors;

converting the measured dV to digital dV measurement signals;

determining and recording monitored corrosion information that is indicative of the respective different amount of corrosion occurring to the exposed first and fourth electrically conductive paths of different corrosion sensor based on the digital dV measurement signals;

then inspecting each corrosion sensor to determine an extent of corrosion that hast occurred to the exposed first and fourth electrically conductive paths of each different corrosion sensors; and then correlating the determined extent of corrosion that hast occurred to the exposed first and fourth electrically conductive paths of each different corrosion sensors with the value of respective monitored corrosion information that has been determined for each different corrosion sensor.

* * * * *